United States Patent [19]

Grotkopp et al.

[11] 4,107,324
[45] Aug. 15, 1978

[54] INDAN-5-YL-N-METHYLCARBAMIC ACID ESTERS

[75] Inventors: Detlef Grotkopp, Duesseldorf; Karlfried Wedemeyer, Cologne; Wolfgang Behrenz, Overath; Ingeborg Hammann, Cologne, all of Fed. Rep. of Germany

[73] Assignee: Bayer Aktiengesellschaft, Leverkusen, Fed. Rep. of Germany

[21] Appl. No.: 763,742

[22] Filed: Jan. 28, 1977

[30] Foreign Application Priority Data

Feb. 2, 1976 [DE] Fed. Rep. of Germany ....... 2603835

[51] Int. Cl.² ...................... C07C 125/06; A01N 9/20
[52] U.S. Cl. ..................................... 424/300; 560/134
[58] Field of Search ................... 260/479 C; 424/300; 560/134

[56] References Cited

U.S. PATENT DOCUMENTS

| 2,870,057 | 1/1956 | Hartle et al. | 260/479 C |
| 3,084,096 | 4/1963 | Lambrech et al. | 260/479 C |
| 3,597,472 | 8/1971 | Heiss et al. | 260/479 C |
| 3,712,915 | 1/1973 | Seyberlich et al. | 260/479 C |

Primary Examiner—Jane S. Myers
Attorney, Agent, or Firm—Burgess, Dinklage & Sprung

[57] ABSTRACT

Indan-5-yl-N-methylcarbamic acid esters of the formula

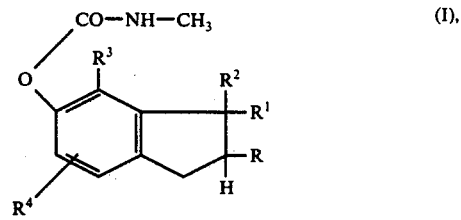

in which
R represents hydrogen or $C_1$-$C_4$ alkyl,
$R^1$ represents hydrogen or $C_1$-$C_4$ alkyl,
$R^2$ represents $C_1$-$C_4$ alkyl,
$R^3$ represents hydrogen or $C_1$-$C_4$ alkyl and
$R^4$ represents hydrogen, chlorine, bromine, $C_1$-$C_4$ alkyl or $C_1$-$C_4$ alkoxy, which possess arthropodicidal and fungicidal properties.

8 Claims, No Drawings

INDAN-5-YL-N-METHYLCARBAMIC ACID ESTERS

The present invention relates to and has for its objects the provision of particular new indan-5-yl-N-methyl-carbamic acid esters which possess arthropodicidal and fungicial properties, active compositions in the form of mixtures of such compounds with solid and liquid dispersible carrier vehicles, and methods for producing such compounds and for using such compounds in a new way especially for combating pests, e.g. insects, acarids and fungi, with other and further objects becoming apparent from a study of the within specification and accompanying examples.

It has been disclosed in U.S. Patent Specifications Nos. 2,870,057 and 3,084,096 that the N-methyl-carbamic acid ester of 5-hydroxyindane (Compound A) is insecticidally active.

The present invention now provides, as new compounds, the indan-5-yl-N-methylcarbamic acid esters of the general formula

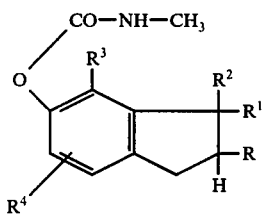

in which
R represents hydrogen or $C_1$–$C_4$ alkyl,
$R^1$ represents hydrogen or $C_1$–$C_4$ alkyl,
$R^2$ represents $C_1$–$C_4$ alkyl,
$R^3$ represents hydrogen or $C_1$–$C_4$ alkyl and
$R^4$ represents hydrogen, chlorine, bromine, $C_1$–$C_4$ alkyl or $C_1$–$C_4$ alkoxy. -C Preferably, R, $R^1$ and $R^3$ each represent hydrogen or alkyl with 1 to 3 carbon atoms, $R^2$ represents alkyl with 1 to 3 carbon atoms, and $R^4$ represents hydrogen, chlorine, bromine, alkyl with 1 to 3 carbon atoms or alkoxy with 1 to 3 carbon atoms.

The indan -5-yl-N-methylcarbamates exhibit a surprisingly powerful insecticidal action and are superior to the previously known N-methylcarbamic acid esters of 5-hydroxyindane even when low amounts are used. The compounds according to the invention thus represent an enrichment of the art.

The present invention also provides a process for the preparation of an indan-5-yl-N-methylcarbamic acid ester of the formula (I) in which
a. a 5-hydroxy-indane of the general formula

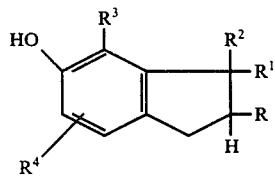

in which
R to $R^4$ have the abovementioned meanings, is reacted with methyl isocyanate, or
b. a 5-hydroxy-indane of the formula (II) is converted, in a first stage, to the chlorocarbonic acid ester by means of an excess of phosgene, and this ester is reacted, in a second stage, with methylamine, or
c. a 5-hydroxy-indane of the formula (II) is reacted, in a first stage, with the equivalent amount of phosgene to give the corresponding bis-(indanyl) carbonate and the latter is split, in a second stage, by means of methylamine.

If 3,3-dimethyl-5-hydroxyindane and methyl isocyanate are used as starting materials, the course of the reaction according to process variant (a) can be represented by the following equation:

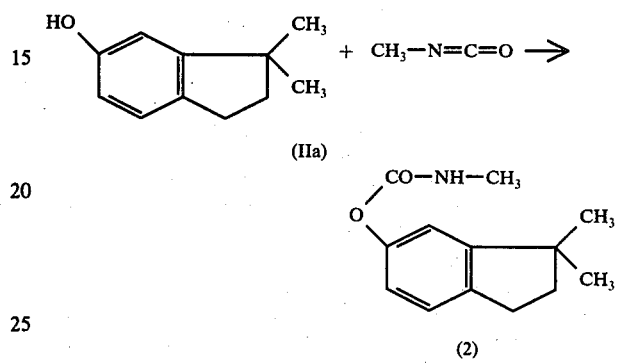

The reaction in process variant (a) can be carried out in an inert solvent. Examples of suitable solvents are hydrocarbons, such as benzine and benzene, chlorinated hydrocarbons, such as chlorobenzene, and ethers, such as dioxane; mixtures of these solvents can also be used. The reaction can be catalyzed by adding a tertiary amine, for example triethylamine or diazabicyclooctane. The reaction temperatures can be varied over a fairly wide range. In general, however, the reaction will be carried out at between 0° and 150° C.

If 3,3-dimethyl-5-hydroxyindane, phosgene and methylamine are used as starting materials, the course of the reaction according to process variant (b) can be represented by the following equation:

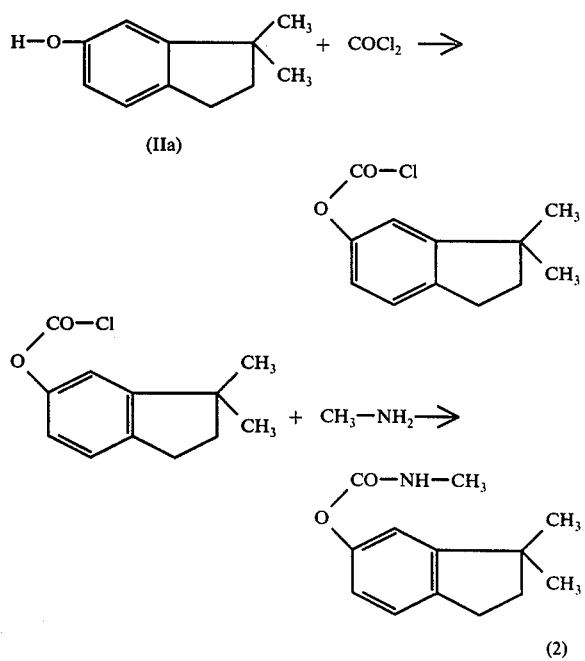

In the first stage of process variant (b), the 5-hydroxy-indane, advantageously in the presence of an inert solvent, such as an aromatic, optionally chlorinated, hydrocarbon, for example benzene, toluene, xylene or chlorobenzene, is converted by means of an excess of phosgene to the chlorocarbonic acid ester, in which reaction the hydrochloric acid formed is usually bound by dropwise addition of a base, advantageously sodium hydroxide, and the pH value of the reaction solution is thus kept above 7. In general, the reaction will be carried out at a reaction temperature of between −10° and +10° C.

In the second stage, the chlorocarbonic acid ester is reacted, either after isolation or directly in the reaction solution obtained, with the equivalent amount of methylamine. This reaction is also advantageously carried out in the presence of an inert solvent, such as aromatic and aliphatic, optionally chlorinated hydrocarbons, such as benzene, toluene, chlorobenzene, benzine or carbon tetrachloride, or ethers, such as dioxane. The reaction temperatures can again be varied within a fairly wide range, but, in general, the reaction is carried out at between −10° and +10° C.

If 3,3-dimethyl-5-hydroxyindane, an equivalent amount of phosgene and methylamine are used as starting materials, the course of the reaction according to process variant (c) can be represented by the following equation:

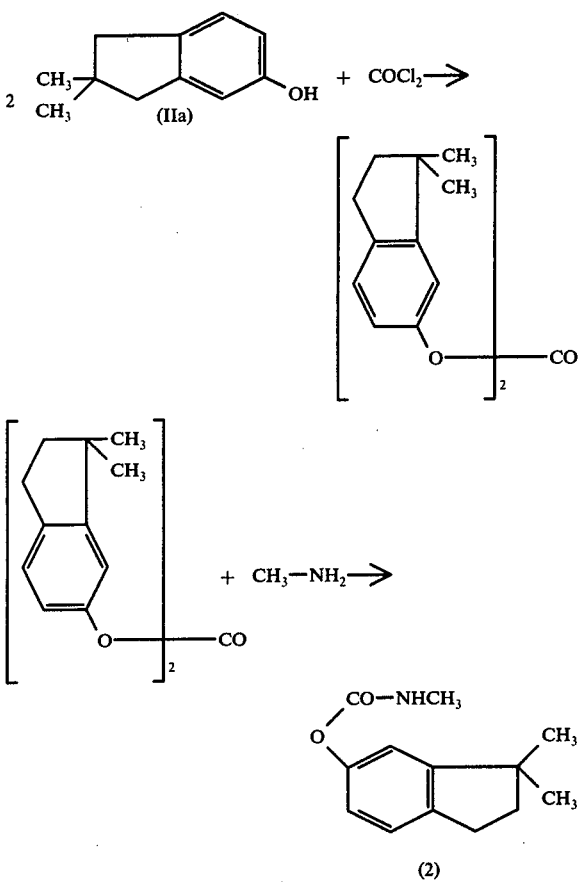

In the first stage of process variant (c), the 5-hydroxyindane is reacted with the equivalent amount of phosgene to give the bis-(indanyl)carbonic acid ester. The reaction is advantageously carried out in an inert solvent, such as an aromatic hydrocarbon, for example benzene or toluene, the hydrochloric acid formed usually being bound by adding a base, preferably an alkali metal hydroxide. The pH value of the reaction solution should be approximately 8. The reaction temperature can vary within a fairly wide range, but it is preferably between 20° and 60° C.

The bis-(5-indanyl) carbonate formed in the first stage is split by means of methylamine. This reaction is advantageously carried out without solvents. However, the reaction can also be carried out in solvents. The most advantageous temperatures are between −10° and +20° C.

Amongst the 5-hydroxy-indanes used as starting materials, 3,3-dimethyl-5-hydroxy-indane, 3,3-dimethyl-5-hydroxy-6-methoxyindane and 4,6-diisopropyl-3,3-dimethyl-5-hydroxy indane have already been disclosed (see Journal of Organic Chemistry of the USSR, volume 1, 2,233–2,242 (1965) and volume 6, 1,245–1,255 (1970) and German Offenlegungsschrift (German Published Specification) 1,801,662). The processes for the preparation of these compounds are applicable to a large number of other 5-hydroxy-indanes. Thus, for example, 3,3,6-trimethyl-5-hydroxy-indane and 3,3,4-trimethyl-5-hydroxy-indane are obtained by reacting o-cresol with isoprene in the presence of phosphoric acid. Similarly, 2,3,3-trimethyl-5-hydroxyindane can be prepared from phenol and 2,3-dimethyl-1,3-butadiene.

Halogen derivatives of the 5-hydroxy-indanes, such as 6-bromo- and 6-chloro-3,3-dimethyl-5-hydroxyindane can be prepared in a known manner by halogenating 3,3-dimethyl-5-hydroxy-indane.

3-Alkyl-5-hydroxy-indanes, such as 3-ethyl-5-hydroxyindane, are accessible by a Grignard reaction of 6-methoxy-1-oxo-indane, which latter compound is already known.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the *Isopoda*, for example *Oniscus asellus*, *Armadillidium vulgare* and *Porcellio scaber*; from the class of the *Diplopoda*, for example *Blaniulus guttulatus*; from the class of the *Chilopoda*, for example *Geophilus carpophagus* and *Scutigera* spec.; from the class of the *Symphyla*, for example *Scutigerella immaculata*; from the order of the *Thysanura*, for example *Lepisma saccharina*; from the order of the *Collembola*, for example *Onychiurus armatus*; from the order of the *Orthoptera*, for example *Blatta orientalis*, *Periplaneta americana*, *Leucophaea maderae*, *Blattella germanica*, *Acheta domesticus*, *Gryllotalpa* spp., *Locusta migratoria migratorioides*, *Melanoplus differentialis* and *Schistocerca gregaria*; from the order of the *Dermaptera*, for example *Forficula auricularia*; from the order of the *Isoptera*, for example *Reticulitermes* spp.; from the order of the *Anoplura*, for example *Phylloxera vastatrix*, *Pemphigus* spp., *Pediculus humanus corporis*, *Haematopinus* spp. and *Linognathus* spp.; from the order of the *Mallophaga*, for example *Trichodectes* spp. and *Damalinea* spp.; from the order of the *Thysanoptera*, for example *Hercinothrips femoralis* and *Thrips tabaci*; from the order of the *Heteroptera*, for example *Eurygaster* spp., *Dysdercus intermedius*, *Piesma*

*quadrata, Cimex lectularius, Rhodnius prolixus* and *Triatoma* spp.; from the order of the *Homoptera*, for example *Aleurodes brassicae, Bomisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera*, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichloplusia Ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera*, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilis surinamensis,* Anthonomus spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus holoeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera*, for example *Diprion* spp., *Hoplocampa* spp., *Lasius* spp., *Monomorium pharaonis* and *Vespa* spp.; from the order of the *Diptera*, for example *Aëdes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera*, for example *Xenopsylla cheopis* and *Ceratophyllus* spp..

The active compounds at the same time also possess a certain fungicidal activity.

When used against pests harmful to health and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally enert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polyketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle dimameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, e.g. to a growing crop, to an area where a crop is to be grown or to a domestic animal, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% meant that all the caterpillars were killed, whereas 0% meant that none of the caterpillars were killed.

The active compounds, the concentrations of the active compounds, the evaluation times and the results can be seen from the following table:

Table 1

(Insects which damage plants)
*Plutella* test

| Active compounds | Active compound concentration in % | Degree of destruction in % after 3 days |
|---|---|---|
| 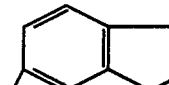 (known) (A) | 0.1<br>0.01 | 55<br>0 |
| 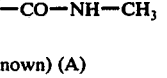 (2) | 0.1<br>0.01 | 100<br>100 |
|  (8) | 0.1<br>0.01 | 100<br>65 |
| 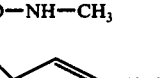 (3) | 0.1<br>0.01 | 100<br>100 |
|  (7) | 0.1<br>0.01 | 100<br>65 |
| 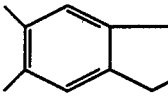 (6) | 0.1<br>0.01 | 100<br>100 |
| 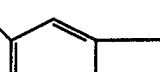 (5) | 0.1<br>0.01 | 100<br>95 |
| 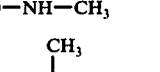 (9) | 0.1<br>0.01 | 100<br>100 |

Table 1-continued (Insects which damage plants)
*Plutella* test

| Active compounds | Active compound concentration in % | Degree of destruction in % after 3 days |
|---|---|---|
| 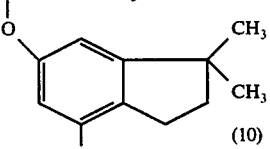 (10) | 0.1<br>0.01 | 100<br>70 |

EXAMPLE 2

Myzus test (contact action)
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% meant that all the aphids were killed, whereas 0% meant that none of the aphids were killed.

The active compounds, the concentrations of the active compounds, the evaluation times and the results can be seen from the following table:

Table 2

(Insects which damage plants)
*Myzus* test

| Active compounds | Active compound concentration in % | Degree of destruction in % after 1 day |
|---|---|---|
| 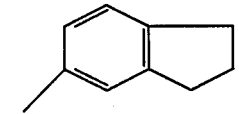 (known) (A) | 0.1 | 0 |
| 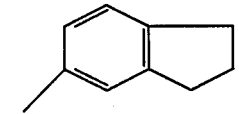 (3) | 0.1<br>0.01 | 100<br>99 |
| 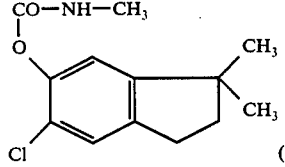 (4) | 0.1<br>0.01 | 100<br>90 |

EXAMPLE 3

Mosquito larvae test
Test insects: *Aëdes aegypti*
Solvent: 99 parts by weight of acetone
Emulsifier: 1 part by weight of benzylhydroxydiphenyl polyglycol ether To produce a suitable preparation of active compound, 2 parts by weight of the active compound were dissolved in 1,000 parts by volume of the solvent containing the amount of emulsifier stated above. The solution thus abtained was diluted with water to the desired lower concentrations.

The aqueous preparations of the active compounds were placed in glass vessels and about 25 mosquito larvae were then placed in each glass vessel.

After 24 hours, the degree of destruction was determined as a percentage: 100% meant that all the larvae were killed. 0% meant that no larvae at all were killed.

The active compounds, the concentrations of the active compounds and the results can be seen from the following table:

Table 3

Mosquito larvae test

| Active compound | Active compound concentration of the solution in ppm | Degree of destruction in % |
|---|---|---|
| known:<br>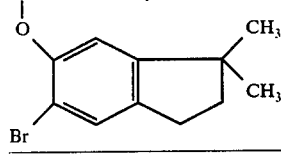 (A) | 10 | 0 |
| according to the invention:<br>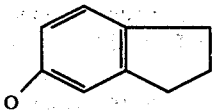 (2) | 1 | 100 |
| 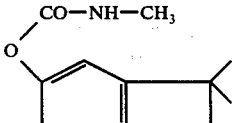 (1) | 1 | 100 |
| 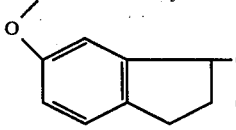 (8) | 10 | 100 |
| 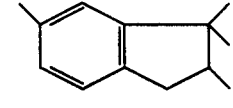 (5) | 10 | 100 |

Table 3-continued

Mosquito larvae test

| Active compound | Active compound concentration of the solution in ppm | Degree of destruction in % |
|---|---|---|
| 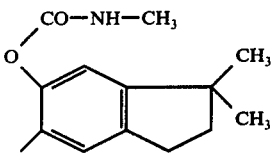 (3) | 10 | 100 |

EXAMPLE 4

LD$_{100}$ test
Test insects: *Sitophilus granarius*
Solvent: Acetone 2 parts by weight of the active compound were taken up in 1,000 parts by volume of the solvent. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects were observed 3 days after the commencement of the experiments. The destruction, in %, was determined. 100% denoted that all the test insects had been killed; 0% denoted that no test insects had been killed.

The active compounds, the concentrations of the active compounds and the results can be seen from the following table:

Table 4

LD$_{100}$ test

| Active compounds | Active compound concentrations % strength solution | Destruction in % |
|---|---|---|
| known: | | |
| 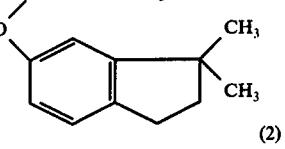 (A) | 0.2 | 0 |
| according to the invention: | | |
| 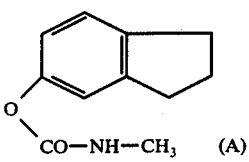 (2) | 0.02 | 100 |

Table 4-continued

LD$_{100}$ test

| Active compounds | Active compound concentrations % strength solution | Destruction in % |
|---|---|---|
| 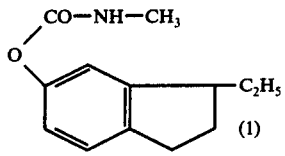 (1) | 0.2 | 100 |
| 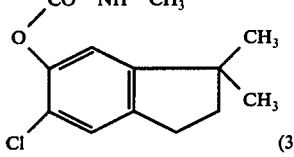 (3) | 0.2 | 100 |

The process of the present invention is illustrated in and by the following preparative examples:

EXAMPLE 5 a. 3-Ethyl-5-hydroxy-indane was prepared as follows:

65 g of 5-methoxy-indan-3-one in 390 ml of tetrahydrofuran were added, over the course of 3 hours, to a Grignard solution of 55 g of ethyl bromide and 12 g of magnesium filings in 175 ml of diethyl ether at room temperature. After boiling for 1.5 hours under reflux, the mixture was poured onto ice. The batch was then extracted by shaking with saturated ammonium chloride solution. The aqueous phase was separated off and extracted twice with tetrahydrofuran. The organic phases were combined and then dried, and the solvent was stripped off. 74 g of residue were obtained, and were dissolved in 260 ml of glacial acetic acid. After adding 4 g of 5% strength palladium-on-charcoal and 26 drops of concentrated hydrochloric acid, hydrogenation was carried out in an autoclave at room temperature under a pressure of 2-3 kg/cm$^2$. The hydrogen uptake had ended after about 16 hours. The contents of the autoclave were suction-filtered and freed from glacial acetic acid. The residue was dissolved in toluene and the solution was washed with water and dried. After removing the solvent, a residue of 53 g was left, which essentially consisted of 3-ethyl-5-methoxy-indane.

A mixture of 41 g of 3-ethyl-5-methoxy-indane and 111 g of pyridine hydrochloride was heated for 5 hours at 210° C. After it had cooled, 800 ml of water were added. The aqueous phase was extracted by shaking with chloroform. The combined organic phases were washed until neutral, and dried. Molecular distillation gave 32 g of 3-ethyl-5-hydroxy-indane; boiling point : 144° C/10 mm Hg.

b) 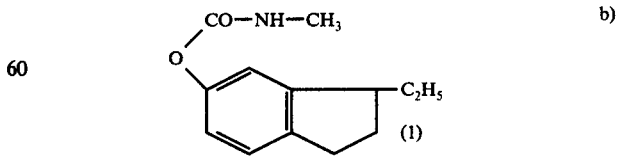

30 g of 3-ethyl-5-hydroxy-indane were dissolved in 150 ml of ligroin at room temperature and 10 drops of triethylamine and 21 g of methyl isocyanate were added. After boiling for three hours under reflux, the reaction solution was allowed to cool and was poured onto ice. The crystals which hereupon precipitated were filtered off and recrystallized from ligroin.

Yield: 35 g. Melting point 79°–80° C.

EXAMPLE 6 a. 3,3-Dimethyl-5-hydroxy-indane was prepared as follows:

322 g of isoprene, stabilized with 1 g of phenothiazine, were added dropwise over the course of 8 hours to a solution of 403 g of phenol, 50 g of 85% strength phosphoric acid and 9 ml of water in 2.14 liters of xylene at 110° C. To complete the reaction, the mixture was stirred overnight at 110° C. The acid phase was separated off and the organic phase was washed until neutral. Fractional distillation gave 230 g of 3,3-dimethyl-5-hydroxy-indane, boiling point 132°–134° C/10 mm Hg; melting point 84.5° –86.5° C.

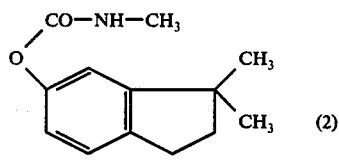

30 g of 3,3-dimethyl-5-hydroxy-indane were dissolved in 150 ml of ligroin at room temperature and 10 drops of triethylamine and 21 g of methyl isocyanate were added. After boiling for three hours under reflux, the reaction solution was allowed to cool and was then poured onto ice. The crystals which thereupon precipitated were filtered and recrystallized twice from ligroin.

Yield: 37 g; melting point 124.5° – 126° C.

EXAMPLE 7 a. 6-Chloro-3,3-dimethyl-5-hydroxy-indane was prepared as follows:

81 g of 3,3-dimethyl-5-hydroxy-indane were dissolved in 162 g of glacial acetic acid. After adding a few grains of iodine, 68 g of sulfuryl chloride were added dropwise over the course of about 1 hour at 40°–45° C. The mixture was then warmed to 50° C for 2 hours. The reaction solution was poured into about 1.5 liters of water. The oil which separated out was taken up in chloroform and separated off. The aqueous phase was repeatedly extracted with chloroform. The combined organic phases were washed until neutral, and concentrated. Fractional distillation gave 54 g of 6-chloro-3,3-dimethyl-5-hydroxy-indane; boiling point 134°–36° C/12 mm Hg.

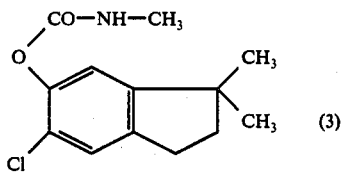

35 g of 6-chloro-3,3-dimethyl-5-hydroxy-indane were dissolved in 175 ml of ligroin at room temperature and 12 drops of triethylamine and 25 g of methyl isocyanate were added. After boiling for two hours under reflux, the reaction solution was allowed to cool and was poured onto ice. The crystals which thereupon precipitated were filtered off and recrystallized from ligroin.

Yield: 39 g. Melting point 115.5° – 117° C.

EXAMPLE 8 a. 6-Bromo-3,3-dimethyl-5-hydroxy-indane was prepared as follows:

128 g of bromine in 100 ml of carbon tetrachloride were added dropwise over the course of 4.5 hours to a solution of 162 g of 3,3-dimethyl-5-hydroxy-indane in 400 ml of carbon tetrachloride at −9° to −2° C. The reaction solution was left to stand overnight at room temperature. It was then washed until neutral, and dried. Fractional distillation gave 139 g of 6-bromo-3,3-dimethyl-5-hydroxy-indane; boiling point: 141.5° C/10 mm Hg.

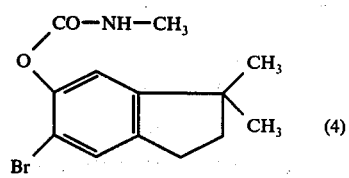

32 g of 6-bromo-3,3-dimethyl-5-hydroxy-indane were dissolved in 150 ml of ligroin at room temperature and 10 drops of triethylamine and 15 g of methyl isocyanate were added. After boiling for 3 hours under reflux, the reaction solution was allowed to cool and was then stirred with ice water. Thereupon, crystals slowly precipitated, and these were filtered off and recrystallized from ligroin.

Yield: 31g: melting point 88.5° – 90.5° C.

EXAMPLE 9 a. 3,3,6-Trimethyl-5-hydroxy-indane was prepared as follows:

370 g of isoprene, stabilized with 1 g of phenothiazine, were added dropwise over the course of 6 hours to a solution of 535 g of o-cresol, 63 g of 85% strength phosphoric acid and 5 ml of water in 1.2 liters of xylene at 110° C. To complete the reaction, stirring was continued overnight at 110° C. The acid phase was separated off and extracted with toluene. The combined organic phases were washed until neutral. Fractional distillation gave 270 g of 3,3,6-trimethyl-5-hydroxy-indane (boiling point: 142°–143° C/12 mm Hg; melting point: 70° – 71° C) and 179 g of 3,3,4-trimethyl-5-hydroxy-indane (boiling point: 146° C/12 mm Hg; melting point 92° – 93° C).

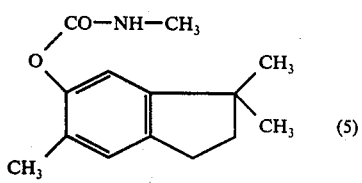

34 g of 3,3,6-trimethyl-5-hydroxy-indane were dissolved in 166 ml of ligroin at room temperature and 12 drops of triethylamine and 22 g of methyl isocyanate were added. After boiling for two hours under reflux, the reaction solution was allowed to cool and was stirred with ice water. Thereupon crystals precipitated, which were filtered off and recrystallized from toluene.

Yield: 27 g; melting point 126.5° – 127.5° C.

EXAMPLE 10

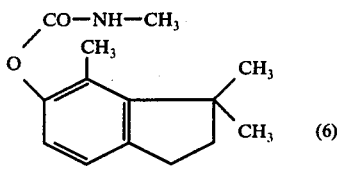

34 g of 3,3,4-trimethyl-5-hydroxy-indane, prepared as described in Example 9, were dissolved in 166 ml of ligroin at room temperature and 12 drops of triethylamine and 22 g of methyl isocyanate were added. After boiling for two hours, the reaction solution was allowed to cool and was stirred with ice water. Thereupon crystals slowly precipitated, and were filtered off and recrystallized from ligroin.

Yield: 39 g; melting point 108° – 109.5° C.

EXAMPLE 11 a. 3,3-Dimethyl-5-hydroxy-6-methoxy-indane was prepared as follows:

449 g of isoprene, stabilized with 1.4 g of phenothiazine, were added dropwise over the course of 6 hours to a solution of 744 g of guaiacol, 76 g of 85% strength phosphoric acid and 6 ml of water in 1.4 liters of xylene at 110° C. To complete the reaction, stirring of the mixture was continued overnight at 110° C. The acid phase was separated off and extracted by shaking with toluene. The combined organic phases were washed until neutral. Fractional distillation gave 443 g of 3,3-dimethyl-5-hydroxy-6-methoxy-indane, boiling point: 145–46° C/12 mm Hg, melting point 43.5° – 44.5° C.

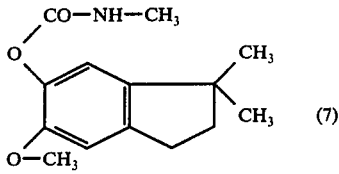

39 g of 3,3-dimethyl-5-hydroxy-6-methoxy-indane were dissolved in 250 ml of ligroin at room temperature and 10 drops of triethylamine and 23 g of methyl isocyanate were added. After boiling for 2 hours under reflux, the reaction solution was left to stand overnight and was stirred with ice water. Thereupon crystals precipitated, which were filtered off and recrystallized three times from toluene.

Yield: 19 g; melting point 129.5° –130° C.

EXAMPLE 12 a. 2,3,3-Trimethyl-5-hydroxy-indane was prepared as follows:

90 g of 2,3-dimethyl-1,3-butadiene, stabilized with 0.2 g of phenothiazine, were added dropwise over the course of 7 hours to a solution of 94 g of phenol, 13 g of 85% strength phosphoric acid and 1 ml of water in 240 ml of xylene at 110° C. To complete the reaction, stirring was continued overnight at 110° C. The acid phase was separated off and extracted by shaking with toluene. The combined organic phases were washed until neutral. Fractional distillation gave 72 g of 2,3,3-trimethyl-5-hydroxy-indane; boiling point: 148° C/12 mm Hg; melting point 66° – 67° C.

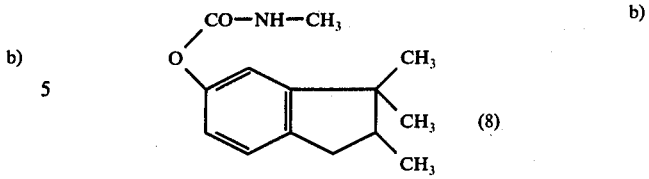

34 g of 2,3,3-trimethyl-5-hydroxy-indane were dissolved in 166 ml of ligroin at room temperature and 12 drops of triethylamine and 22 g of methyl isocyanate were added. After boiling for two hours under reflux, the reaction solution was allowed to cool, and was stirred with ice-water. Thereupon crystals precipitated, which were filtered off and recrystallized from toluene.

Yield: 36 g; melting point 118.5° – 119.5° C.

EXAMPLE 13 a. 3,3,7-Trimethyl-5-hydroxy-indane was prepared as follows:

449 of isoprene, stabilized with 1.35 g of phenothiazine, were added dropwise over the course of 7 hours to a solution of 648 g of m-cresol, 77 g of 85% strength phosphoric acid and 6 ml of water in 1.44 liters of xylene at 110° C. To complete the reaction, stirring was continued overnight at 110° C. After cooling, the acid phase was separated off and extracted by shaking with toluene. The combined organic phases were washed until neutral. Fractional distillation gave 252 g of 3,3,7-trimethyl-5-hydroxy-indane; boiling point 151°–155° C/18 mm Hg; melting point 80° – 81° C.

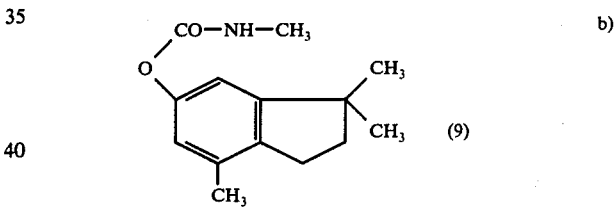

45 g of 3,3,7-trimethyl-5-hydroxy-indane were dissolved in 220 ml of ligroin at room temperature and 15 drops of triethylamine and 29 g of methyl isocyanate were added. After boiling for three hours under reflux, the mixture was allowed to cool and the crystals which had precipitated were filtered off, washed with water, dried and recrystallized from toluene.

Yield: 39 g; melting point 123–24° C.

EXAMPLE 14 a. 7-Chloro-3,3-dimethyl-5-hydroxy-indane was prepared as follows:

449 g of isoprene, stabilized with 1.35 g of phenothiazine, were added dropwise over the course of 5.5 hours to a solution of 771 g of m-chlorophenol, 77 g of 85% strength phosphoric acid and 6 ml of water in 1.44 liters of o-dichlorobenzene at 150° C. To complete the reaction, stirring was continued overnight at 150° C. After cooling, the acid phase was separated off and extracted by shaking with toluene. The combined organic phases were washed until neutral. Fractional distillation gives 194 g of 7-chloro-3,3-dimethyl-5-hydroxy-indane; boiling point 105°–110° C/0.5 mm Hg; melting point 86.5° – 87.5° C.

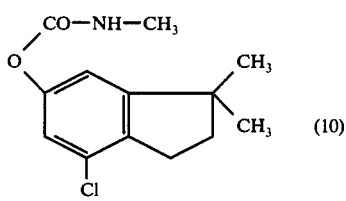

(10)

b) 40 g of 7-chloro-3,3-dimethyl-5-hydroxy-indane were dissolved in 200 ml of ligroin at room temperature and 15 drops of triethylamine and 29 g of methyl isocyanate were added. After boiling for about 2.5 hours under reflux, the reaction solution was left to cool overnight, and was stirred with ice-water. Thereupon crystals precipitated, which were filtered off and recrystallized from toluene.

Yield: 41 g; melting point 128°–129.5° C.

Other compounds which can be similarly prepared include: 3,4,6-Triisopropyl-indan-5-yl-N-methylcarbamic acid ester (11) 3-isopropyl-6-isopropoxy-indan-5-yl-N-methylcarbamic acid ester (12) and the like.

It will be appreciated that the instant specification and examples are set forth by way of illustration and not limitation, and that various modifications and changes may be made without departing from the spirit and scope of the present invention.

What is claimed is:

1. An indan-5-yl-N-methylcarbamic acid ester of the formula

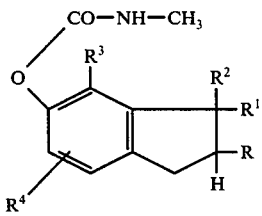

in which

R and $R^1$ represent hydrogen or $C_1$–$C_4$-alkyl, $R^2$ represents $C_1$–$C_4$-alkyl, $R^3$ represents hydrogen or $C_1$–$C_4$-alkyl, and $R^4$ represents hydrogen, chlorine, bromine, $C_1$–$C_4$ alkyl or $C_1$–$C_4$ alkoxy.

2. A compound according to claim 1, in which R, $R^1$ and $R^3$ each independently represents hydrogen or alkyl with 1 to 3 carbon atoms, $R^2$ represents alkyl with 1 to 3 carbon atoms, and $R^4$ represents hydrogen, chlorine, bromine, alkyl with 1 to 3 carbon atoms or alkoxy with 1 to 3 carbon atoms.

3. The compound according to claim 1 wherein such compound is 3-ethyl-indan-5-yl-N-methylcarbamic acid ester of the formula

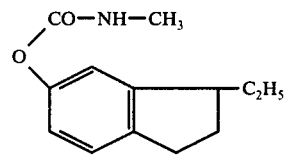

4. The compound according to claim 1 wherein such compound is 3,3-dimethyl-indan-5-yl-N-methylcarbamic acid ester of the formula

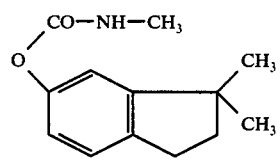

5. The compound according to claim 1 wherein such compound is 6-chloro-3,3-dimethyl-indan-5-yl-N-methylcarbamic acid ester of the formula

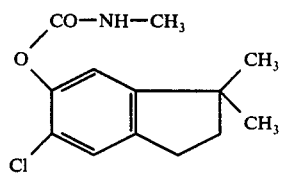

6. An arthropodicidal composition containing as active ingredient an arthropodicidally effective amount of a compound according to claim 1 in admixture with a diluent.

7. A method of combating arthropods which comprises applying to the arthropods, or to a habitat thereof, an arthropodicidally effective amount of a compound according to claim 1.

8. The method according to claim 7 in which said compound is
3-ethyl-indan-5-yl-N-methylcarbamic acid ester,
3,3-dimethyl-indan-5-yl-N-methylcarbamic acid ester, or
6-chloro-3,3-dimethyl-indan-5-yl-N-methylcarbamic acid ester.

* * * * *